(12) United States Patent
Srivastava et al.

(10) Patent No.: US 8,785,483 B2
(45) Date of Patent: Jul. 22, 2014

(54) METHODS FOR TREATING COPD

(75) Inventors: Satish K. Srivastava, Galveston, TX (US); Kota V. Ramana, Galveston, TX (US); Umesh Yadav, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 104 days.

(21) Appl. No.: 13/336,833

(22) Filed: Dec. 23, 2011

(65) Prior Publication Data

US 2012/0238609 A1 Sep. 20, 2012

Related U.S. Application Data

(60) Provisional application No. 61/426,788, filed on Dec. 23, 2010.

(51) Int. Cl.
*A61K 31/41* (2006.01)
*A01N 43/78* (2006.01)
*A61K 31/335* (2006.01)

(52) U.S. Cl.
USPC .......................... 514/360; 514/367; 514/450

(58) Field of Classification Search
USPC .......................................... 514/360, 367, 450
See application file for complete search history.

(56) References Cited

U.S. PATENT DOCUMENTS

| | | | |
|---|---|---|---|
| 6,127,367 A | 10/2000 | Beyer et al. | |
| 6,380,200 B1 | 4/2002 | Mylari et al. | |
| 6,696,407 B1 | 2/2004 | Longo et al. | |
| 2004/0047919 A1 | 3/2004 | Srivastava et al. | |
| 2006/0110814 A1 | 5/2006 | Srivastava et al. | |
| 2006/0210651 A1 | 9/2006 | Srivastava et al. | |
| 2006/0293265 A1 | 12/2006 | Srivastava et al. | |
| 2007/0021366 A1 | 1/2007 | Srivastava et al. | |
| 2009/0270490 A1 | 10/2009 | Srivastava et al. | |
| 2010/0016404 A1 | 1/2010 | Srivastava et al. | |
| 2010/0022625 A1 | 1/2010 | Srivastava et al. | |
| 2010/0144748 A1 | 6/2010 | Srivastava | |
| 2011/0092566 A1 | 4/2011 | Srivastava et al. | |

OTHER PUBLICATIONS

CDC—Fact Sheet—Health Effects of Cigarette Smoking. Updated Aug. 1, 2013. pp. 1-5.*
Barisani, et al., FEBS Lett., 2000, pp. 208-212, vol. 469(2-3).
Bhatnagar, Aruni, et al., "Aldose reductase: Congenial and injurious profiles of an enigmatic enzyme", Biochem Med Metab Biol., Oct. 1992, pp. 91-121, vol. 48(2).
Dixit, et al., "Kinetic and Structural Characterization of the Glutathione-binding Site of Aldose Reductase", J. Biol. Chem., Jul. 14, 2000, pp. 21587-21595, vol. 275(28).
Jagt, David L., et al., "Substrate specificity of human aldose reductase: identification of 4-hydroxynonenal as an endogenous substrate", Biochem Biophys Acta., Jun. 12, 1995, pp. 117-126, vol. 1249(2).
Nakamura, et al., Free Radic. Biol. Med., 2000, pp. 17-25, vol. 29(1).
O'Connor, et al., "Major differences exist in the function and tissue-specific expression of human aflatoxin B1 aldehyde reductase and the principal human aldo-keto reductase AKR1 family members", Biochem. J., 1999, pp. 487-504, vol. 343 Pt. 2.
Ramana, et al., "Selective Recognition of Glutathiolated Aldehydes by Aldose Reductase", Biochemistry, 2000, pp. 12172-12180, vol. 39.
Rittner, et al., "Aldose reductase functions as a detoxification system for lipid peroxidation products in vasculitis", J. Clin. Invest., 1999, pp. 1007-1013, vol. 103(7).
Ruef, et al., "Involvement of Aldose Reductase in Vascular Smooth Muscle Cell Growth and Lesion Formation After Arterial Injury", Arterioscler. Thromb. Vasc. Biol., 2000, pp. 1745-1752, vol. 20(7).
Seo, et al., "Lipoprotein Lipase-mediated Selective Uptake from Low Density Lipoprotein Requires Cell Surface Proteoglycans and Is Independent of Scavenger Receptor Class B Type 1", J. Biol. Chem., Jun. 1, 2000, pp. 30355-30362, vol. 275(39).
Shinmura, et al., Proc. Natl. Acad. Sci. USA, 2000, pp. 10197-10202, vol. 97(18).
Spycher, et al., "Aldose reductase induction: a novel response to oxidative stress of smooth muscle cells", Faseb J., 1997, pp. 181-188, vol. 11(2).x.
Srivastava, S., et al., "Lipid Peroxidation Product, 4-Hydroxynonenal and its Conjugate with GSH Are Excellent Substrates of Bovine Lens Aldose Reductase", Biochem and Biophys Res Commun., Dec. 26, 1995, pp. 741-746, vol. 217(3).
Srivastava, S., et al., "Kinetic studies of a FR-1, a growth factor-inducible aldo-keto reductase", Biochemistry, 1998, pp. 12909-12917, vol. 37(37).
Yabe-Nishimura, Chihiro, "Aldose Reductase in Glucose Toxicity: A Potential Target for the Prevention of Diabetic Complications", Pharmacological Reviews, 1998, pp. 21-33, vol. 50(1).
Yang, et al., "Decreased SLIM1 Expression and Increased Gelsolin Expression in Failing Human Hearts Measured by High-Density Oligonucleotide Arrays", Circulation, 2000, pp. 3046-3052, vol. 102(25).

\* cited by examiner

*Primary Examiner* — Renee Claytor

(57) ABSTRACT

Embodiments of the invention include methods and compositions involving aldose reductase inhibitors for treating COPD.

8 Claims, 10 Drawing Sheets

SEQUENCE LISTING

<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
tccggcctca tcttctcc                                                    18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
acttgggcac tggtgctg                                                    18

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
cgaagtgctc aaggacatcg ag                                        22

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
cggtattggt gctctgtcca ca                                        22

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gaccccttca ttgacctcaa c                                         21

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cataccagga aatgagcttg                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
agaccagact cccctgtgca                                           20

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
tgggtcctgt agatggcatt g                                         21

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 9
tgtgtccgtc gtggatctga                                          20

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
cctgcttcac caccttcttg at                                       22
```

METHODS FOR TREATING COPD

STATEMENT REGARDING FEDERALLY FUNDED RESEARCH

This invention was made with government support under award number 08-0219 awarded by the American Asthma Foundation. The Foundation may have certain rights in the invention.

This application claims priority to U.S. Provisional Application Ser. No. 61/426,788 filed Dec. 23, 2010, which is incorporated herein by reference in its entirety.

BACKGROUND

Embodiments of this invention are related generally to physiology and medicine. More specifically, this invention is related to aldose reductase inhibitors (ARIs) and their use in treating chronic obstructive pulmonary disease (COPD).

Aldose reductase (AR) catalyzes the reduction of a wide range of aldehydes (Bhatnager and Srivastava, *Biochem Med Metab Biol.* 48(2):91-121, 1992). The substrates of the enzyme range from aromatic and aliphatic aldehydes to aldoses such as glucose, galactose, and ribose. The reduction of glucose by AR is particularly significant during hyperglycemia and increased flux of glucose via AR has been etiologically linked to the development of secondary diabetic complications (Bhatnager and Srivastava, *Biochem Med Metab Biol.* 48(2):91-121, 1992; Yabe-Nishimura, *Pharmacol Rev.* 50(1):21-33, 1998). However, recent studies showing that AR is an excellent catalyst for the reduction of lipid peroxidation-derived aldehydes and their glutathione conjugates (Srivastava et al., *Biochem Biophys Res Commun.* 217:741-746, 1995; Vander Jagt et al., *Biochim Biophys Acta.* 1249(2):117-26, 1995; Srivastava et al., *Biochemistry.* 37(37):12909-17, 1998; Srivastava et al., *Adv Exp Med. Biol.* 463:501-7, 1999; Dixit et al., *J Biol. Chem.* 275:21587-21595, 2000; Ramana et al., *Biochemistry.* 39:12172-12180, 2000) suggest that in contrast to its injurious role during diabetes, under normal glucose concentration, AR may be involved in protection against oxidative and electrophilic stress. The antioxidant role of AR is consistent with the observations that in a variety of cell types AR is upregulated by oxidants such as hydrogen peroxide (Spycher et al., *FASEB J.* 11(2):181-8, 1997), lipid peroxidation-derived aldehydes (Ruef et al., *Arterioscler Thromb Vasc Biol.* 20(7):1745-52, 2000; Rittner et al., *J Clin Invest.* 103(7):1007-13, 1999), advanced glycosylation end products (Nakamura et al., *Free Radic Biol Med.* 29(1):17-25, 2000) and nitric oxide (Seo et al., *J Biol. Chem.* 275(39): 30355-62, 2000). The expression of the enzyme is also increased under several pathological conditions associated with increased oxidative or electrophilic stress such as iron overload (Barisani et al., *FEBS Lett.* 469(2-3):208-12, 2000), alcoholic liver disease (O'Connor et al., *Biochem J.* 343 Pt 2:487-504, 1999), heart failure (Yang et al., *Circulation.* 102 (25):3046-52, 2000), myocardial ischemia (Shinmura et al., *Proc Natl Acad Sci USA.* 97(18):10197-202, 2000), vascular inflammation (Rittner et al., *J Clin Invest.* 103(7):1007-13, 1999) and restenosis (Ruef et al., *Arterioscler Thromb Vasc Biol.* 20(7):1745-52, 2000), and various forms of cancer.

Inhibitors of aldose reductase have been indicated for some conditions and diseases, such as diabetes complications, ischemic damage to non-cardiac tissue, Huntington's disease. See U.S. Pat. Nos. 6,696,407, 6,127,367, 6,380,200, which are all hereby incorporated by reference. In some cases, the role in which aldose reductase plays in mechanisms involved in the condition or disease is known. For example, in U.S. Pat. No. 6,696,407 indicates that an aldose reductase inhibitors increase striatal ciliary neurotrophic factor (CNTF), which has ramifications for the treatment of Huntington's Disease. In other cases, however, the way in which aldose reductase or aldose reductase inhibitors work with respect to a particular disease or condition is not known.

Therefore, the role of aldose reductase in a number of diseases and conditions requires elucidation, as patients with these diseases and conditions continue to require new treatments. Thus, there is a need for preventative and therapeutic methods involving aldose reductase and aldose reductase inhibitors.

SUMMARY OF THE INVENTION

Embodiments of the invention are directed to methods of treating chronic obstructive pulmonary disease (COPD) in a subject diagnosed with, exhibiting symptoms of, or at risk of developing COPD by administering a therapeutically effective amount of an aldose reductase inhibitor (ARI). As used herein, a "risk" of developing COPD is based on the subject's medical, personal, and/or family history. In particular, current or previous smoking (most notably cigarettes, but also other nicotine or non-nicotine, e.g., marijuana, products) indicate a risk of developing COPD, but risk factors also include, but are not limited to exposure to smoke or other environmental hazards (e.g., mining or textile industry hazards, fumes, air pollution), genetic susceptibility, autoimmune disease, and bronchial hyperresponsiveness. A subject may also be one that exhibits one or more symptoms of COPD including, but not limited to: chronic cough, sputum production, dyspnea (shortness of breath), rhonchi (rattling breathing sounds), and airway limitation on pulmonary function testing.

In certain aspects, the aldose reductase inhibitor is administered to the patient as a prodrug. Typically, a prodrug is an inactive or less active form of a drug that is metabolized or converted in vivo to an active or more active form.

The ARI can be administered by any route, including orally, endoscopically, intratracheally, intrabronchially, intravenously, intralesionally, intramuscularly, intraperitoneally, percutaneously, or subcutaneously. In certain aspects the ARI is administered orally or by inhalation or instillation, e.g., by inhaler or other aerosol delivery devices.

In certain embodiments the aldose reductase inhibitor is a peptide, a peptide mimetic, a small molecule, or an inhibitory RNA. The aldose reductase inhibitor can be an siRNA or other inhibitory nucleic acid, a carboxylic acid, a hydantoin, a pyridazinone, or a pharmaceutically acceptable derivative thereof. In particular aspects the aldose reductase inhibitor is fidarestat, sorbinil, epalrestat, ponalrestat, methosorbinil, risarestat, imirestat, ALO-1567, quercetin, zopolrestat, AD-5467, NZ-314, M-16209, minalrestat, AS-3201, WP-921, luteolin, tolrestat, EBPC, or a pharmaceutically acceptable derivative thereof. In certain embodiments the aldose reductase inhibitor is fidarestat.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The term "treating" includes treating a physiological cause of disease, treating a condition associated with the disease, and treating one or symptoms of the disease. Treating includes reducing the severity (including any measurable decrease to complete elimination), reducing the frequency, slowing or stopping the progression of, increasing the time until onset, or preventing the onset of one or more disease symptoms.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising", "having", "including", and "containing" are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

Figure 1:
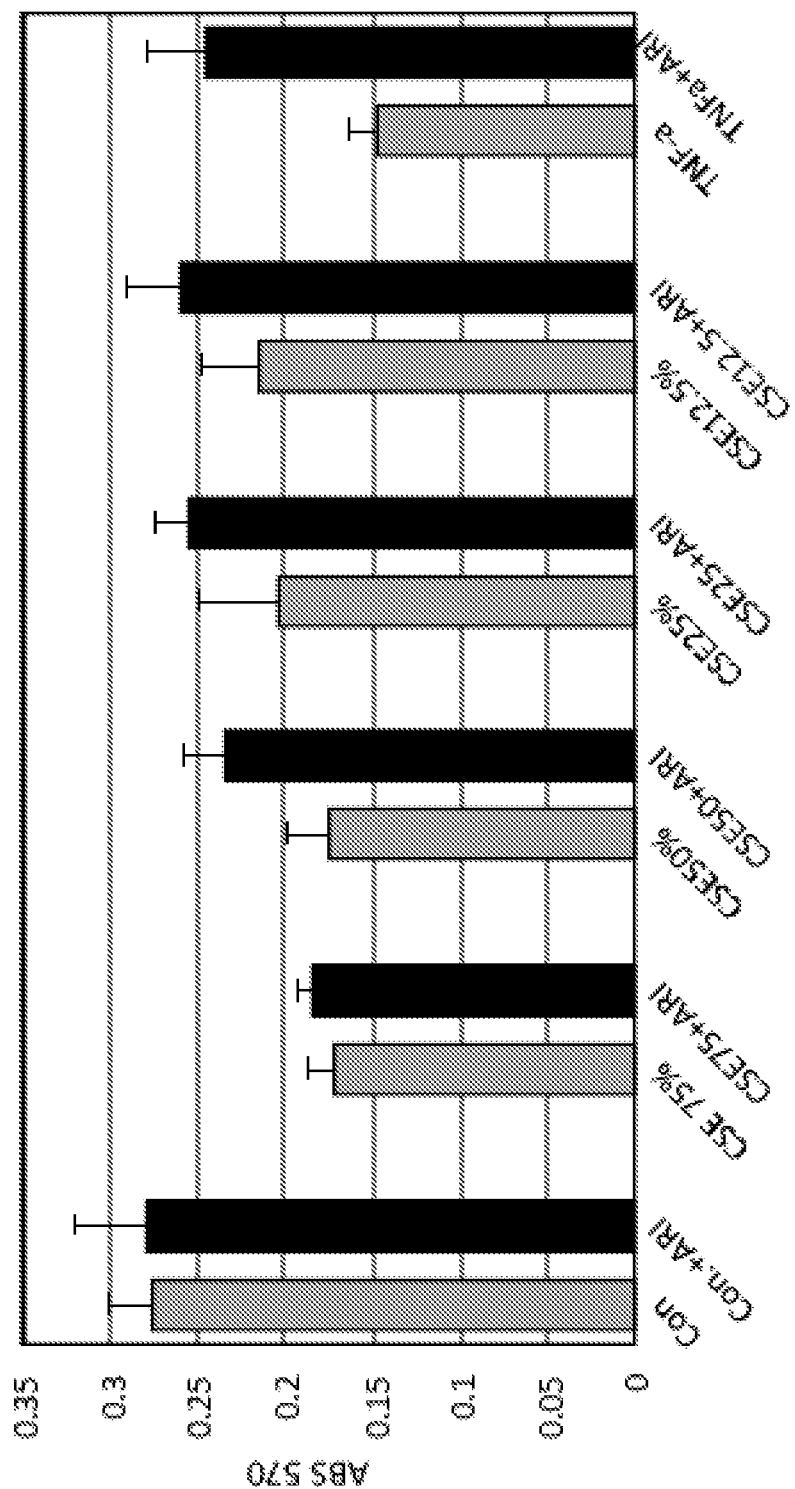
FIG. 1. Inhibition of AR prevents cigarette smoke extract (CSE)-induced cell-death in small airway epithelial cells (SAEC). MTT assay was performed after incubating the cells for 24 h with different concentrations of CSE in absence and presence of 10 µM Fidarestat. Bars (Mean±SD; n=6) represent the absorbance at 570 nm corresponding to live cells.

The inventors have demonstrated that Aldose Reductase (AR) is important for the detoxification of lipid aldehydes. In addition to the detoxification role, AR activity is necessary for cell signaling of cytokines, chemokines, endotoxins, high glucose, and growth factors that cause cell apoptosis and proliferation which cause tissue dysfunction leading to inflammation and various diseases, i.e., AR is an obligatory mediator of cytokine, chemokine, growth factors, and bacterial endotoxin-induced by activation of transcription factors NF-κB and AP1 through a cascade of kinases. The activation of transcription factors is responsible for the synthesis and release of a number of cytokines, chemokines, and growth factors that cause cytotoxicity. They are responsible for causing inflammation in general (see U.S. Pub. 2004/0047919, U.S. Pub. 2006/0293265, and U.S. Pub. 2010/0144748, all of which are hereby incorporated by reference), which is associated with COPD and allergic asthma.

I. ALDOSE REDUCTASE AND COPD

In certain aspects of the invention, an aldose reductase inhibitor (ARI) is used to treat COPD. Chronic obstructive pulmonary disease (COPD), which results from chronic exposure to cigarette smoke, noxious gases and/or particles, is one of the most common reasons of major morbidity and mortality worldwide and afflicts over 600 million people as estimated by World Health Organization. Inflammation of the airway plays a major role in the pathogenesis of COPD, which involves infiltration of inflammatory cells in the airway and the accumulation of inflammatory mucous exudates. The major risk factor in the pathogenesis of COPD is cigarette smoke, which causes airway inflammation by activating resident cells including airway epithelial cells, macrophages, neutrophils, and T-lymphocytes, which generate reactive oxygen species (ROS) and release proteases leading to cellular injury. Production of ROS has been directly linked to oxidation of proteins, DNA, and lipids, which may cause direct lung injury or induce a variety of cellular responses through the generation of secondary metabolic reactive species. The inventors have demonstrated that inhibition of aldose reductase (AR) prevents cigarette smoke extract (CSE)-induced cellular changes in human small airway epithelial cells (SAEC) that are characteristic of COPD including cellular apoptosis, and secretion of cytokines, chemokines, and other inflammatory markers. Aldose reductase (AR), a member of the aldo-keto reductase superfamily, is a cytosolic protein that catalyzes NADPH-dependent reduction of glucose to sorbitol in hyperglycemic conditions, which is implicated in diabetic complications. However evidence has recently been presented indicating that AR is crucial in the oxidative stress-induced molecular signal and that AR catalyzed metabolic product is an excellent mediator of redox signaling that plays an important role in various inflammation-related pathologies such as diabetic complications, cardiovascular diseases, asthma, COPD, cancer, and infectious diseases. The results described herein show that IL-13-induced goblet cell formation is prevented by AR inhibition in-vitro as well as in-vivo. These and present results together suggest that AR inhibition is beneficial in preventing and treating the COPD as it prevented cell-death, cytokines release and mucus formation in human airway epithelial cells.

Aldose reductase (AR), a member of the aldo-keto reductase superfamily, is a cytosolic protein that catalyzes NADPH-dependent reduction of glucose to sorbitol in hyperglycemic conditions, which is implicated in diabetic complications. Evidence has recently been presented indicating that AR is crucial in the oxidative stress-induced molecular signal and that AR catalyzed metabolic product is an excellent mediator of redox signaling. The results described herein show that IL-13-induced goblet cell formation is prevented by AR inhibition in vitro as well as in vivo. These results suggest that AR inhibition is beneficial in preventing and treating the COPD as it prevented cell-death, cytokines release and mucus formation in human airway epithelial cells.

II. ALDOSE REDUCTASE INHIBITORS

An aldose reductase inhibitor is any compound that inhibits the enzyme aldose reductase. Exemplary aldose reductase inhibitors are readily available or can be easily synthesized by those skilled in the art using conventional methods of organic synthesis. Many of these are well known to those of skill in the art, and a number of pharmaceutical grade AR inhibitors are commercially available, such as fidarestat (SNK-860), (2S,4S)-2-aminoformyl-6-fluoro-spiro[chroman-4,4'-imidazolidine]-2',5'-dione (CAS number 136087-85-9); Tolrestat, N-[[6-methoxy-5-(trifluoromethyl)-1-naphthalenyl]thioxomethyl]-N-methylglycine, [Wyeth-Ayerst, Princeton, N.J.; other designations are Tolrestatin, CAS Registry Number 82964-04-3, Drug Code AY-27,773, and brand names ALREDASE (Am. Home) and LORESTAT (Recordati)]; Ponalrestat, 3-(4-bromo-2-fluorobenzyl)-4-oxo-3H-phthalazin-1- ylacetic acid [ICI, Macclesfield, U.K.; other designations are CAS Registry Number 72702-95-5, ICI-128,436, and STATIL (ICI)]; Sorbinil, (S)-6-fluoro-2,3-dihydrospiro[4H-1-benzopyran-4,4'-imidazolidine]-2',5'-di one (Pfizer, Groton, Conn.; CAS Registry Number 68367-52-2, Drug Code CP-45,634); EPALRESTAT (ONO, Japan); METHOSORBINIL (Eisai); ALCONIL (Alcon); AL-1576 (Alcon); CT-112 (Takeda); and AND-138 (Kyorin).

Other ARIs have been described. For a review of ARIs used in the diabetes context, see Humber, "Aldose Reductase Inhibition: An Approach to the Prevention of Diabetes Complications", Porte, ed., Ch. 5, pp. 325-353; Tomlinson et al., 1992), such as spirohydantoins and related structures, spiro-imidazolidine-2',5'-diones; and heterocycloic alkanoic acids. Other aldose reductase inhibitors are ONO-2235; zopolrestat; SNK-860; 5-3-thienyltetrazol-1-yl (TAT); WAY-121,509; ZENECA ZD5522; M16209; (5-(3'-indolal)-2-thiohydantoin; zenarestat; zenarestat 1-O-acylglucuronide; SPR-210; (2S,4S)-6-fluoro-2%5'-dioxospiro-[chroman-4,4'-imidazolidine]-2-carboxamide (SNK-880); arylsulfonylamino acids; 2,7-difluorospirofluorene-9,5'-imidazolidine-2',4'-dione (imiriestat, A111576, HOE 843); isoliquiritigenin; 3,4-dihydro-4-oxo-3-[[5-(trifluoromethyl)-2-benzothiazolyl]methyl]-1-phth-alazineacetic acid; (S)-6-fluorospiro[chroman-4,4'-imidazolidine]-2,5'-dione; N-[(5-trifluoromethyl)-6-methoxy-1-naphthalenyl]thioxomethyl}-N-methylgly-cine; 3-(4-bromo-2-fluorobenzyl)-3,4-dihydro-4-oxo-1-phthala-zineacetic acid; 5-[(Z,E)-.beta.-methylcinnamylidene]-4-oxo-2-thioxo-3-thiazolidene acetic acid; 3-(4-bromo-2-fluorobenzyl)-7-chloro-3,4-dihydro-2,4-dioxo-1(2H)quinazo line acetic acid; 3,4-dihydro-3-oxo-4-[(4,5,7-trifluoro-2-benzothiazolyl)methyl]-2H-1,4-benzothiazine-2-acetic acid; N-[3,5-dimethyl-4-[(nitromethyl)sulfonyl]phenyl]-2-methylbenzeneacetamide; (2S,4S)-6-fluoro-2',5'-dioxospiro (chroman-4,4'-imidazolidine)-2-carboxamide; 2-[(4-bromo-2-fluorophenyl)methyl]-6-fluorospiro[isoquinoline-4(1H),3-'-pyrrolidine]-1,2',3,5'(2'H)-tetrone; 2R,4R-6,7-dichloro-4-hydroxy-2-methylchroman-4-acetic acid; 2R,4R-6,7-dichloro-6-fluoro-4-hydroxy-2-methylchroman-4-acetic acid; 3,4-dihydro-2,8-diisopropyl-3-oxo-2H-1,4-benzoxazine-4-acetic acid; d-2-methyl-6-fluoro-spiro(chroman-4',4'-imidazolidine)-2',5'-dione; 2-fluoro-spiro(9H-fluorene-9,4'-imidazolidine)-2',5'-dione; 2,7-di-fluoro-spiro(9H-fluorene-9,4'-imidazolidine)-2',5'-dione; 2,7-di-fluoro-5-methoxy-spiro(9H-fluorene-9,4'-imidazolidine)-2',5'-dione; 7-fluoro-spiro(5H-indenol[1,2-b]pyridine-5,3'-pyrrolidine)-2,5'-dione; d-cis-6'-chloro-2',3'-dihydro-2'-methyl-spiro-(imidazolidine-4,4'-4'H-pyr-ano(2,3-b)pyridine)-2,5-dione; spiro[imidazolidine-4,5'(6H)-quinoline]-2,5-dione-3'-chloro-7,'8'-dihydro-7'-methyl-(5'-cis); 3,4-dihydro-3-(5-fluorobenzothiazol-2-yl-methyl)-4-oxophthalazin-1-yl-acetic acid; 3-(5,7-difluorobenzothiazol-2-ylmethyl)-3,4-dihydro-4-oxophthala-zin-1-yl-acetic acid; 3-(5-chlorobenzothiazol-2-ylmethyl)-3,4-dihydro-4-oxophthalazin-1-yl-acetic acid; 3-(5,7-dichlorobenzothiazol-2-ylmethyl)-3,4-dihydro-4-oxophthalaz-in-1-yl-acetic acid; 3,4-dihydro-4-oxo-3-(5-trifluoromethylbenzoxazol-2-yl-methyl)phthalazin-1-yl-acetic acid; 3,4-dihydro-3-(5-fluorobenzoxazol-2-ylmethyl)-4-oxophthalazin-1-yl-acetic acid; 3-(5,7-difluorobenzoxazol-2-ylmethyl)-3,4-dihydro-4-oxophthalazin-1-yl-acetic acid; 3-(5-chlorobenzoxazol-2-ylmethyl)-3,4-dihydro-4-oxophthalazin-1-y-lacetic acid; and 3-(5,7-dichlorobenzoxazol-2-ylmethyl)-3,4-dihydro-4-oxophthalazin-1-yl-acetic acid.

In some embodiments, the aldose reductase inhibitor is a compound that directly inhibits the bioconversion of glucose to sorbitol catalyzed by the enzyme aldose reductase. Such aldose reductase inhibitors are direct or specific inhibitors, which are contemplated as part of the invention. Direct inhibition is readily determined by those skilled in the art according to standard assays (Malone, 1980).

In addition to classification by activity, the ARIs can also be classified by chemical structure. In one embodiment, the ARI is a carboxylic acid, a hydantoin, a pyridazinone, or a pharmaceutically acceptable derivative thereof. In some embodiments, the ARI is a synthetic chemical compound. Alternatively, the ARI is a naturally-derived compound (e.g., plant extracts or endogenous antioxidants that inhibit aldose reductase).

The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. Nos. 4,251,528; 4,600,724; 4,464,382, 4,791, 126, 4,831,045; 4,734,419; 4,883,800; 4,883,410; 4,883,410; 4,771,050; 5,252,572; 5,270,342; 5,430,060; 4,130,714; 4,540,704; 4,438,272; 4,436,745, 4,438,272; 4,436,745, 4,438,272; 4,436,745, 4,438,272; 4,980,357; 5,066,659; 5,447,946; and 5,037,831.

In addition to the aldose reductase inhibitors specifically described herein, other aldose reductase inhibitors will be known to those skilled in the art. Also, common chemical names or other designations are in parentheses where applicable, together with reference to appropriate patent literature disclosing the compound. Accordingly, examples of aldose reductase inhibitors useful in the compositions, methods and kits of this invention include, but are not limited to: 3-(4-bromo-2-fluorobenzyl)-3,4-dihydro-4-oxo-1-phthala-zineacetic acid (ponalrestat, U.S. Pat. No. 4,251,528); N[[(5-trifluoromethyl)-6-methoxy-1-naphthalenyl]thioxomethyl}-N-methylglycine (tolrestat, U.S. Pat. No. 4,600,724); 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045); 3-(4-bromo-2-fluorobenzyl)-7-chloro-3,4-dihydro-2,4-dioxo-(2H)-quinazolineacetic acid (zenarestat, U.S. Pat. No. 4,734, 419, and U.S. Pat. No. 4,883,800); 2R,4R-6,7-dichloro-4-hydroxy-2-methylchroman-4-acetic acid (U.S. Pat. No. 4,883,410); 2R,4R-6,7-dichloro-6-fluoro-4-hydroxy-2-methylchroman-4-acetic acid (U.S. Pat. No. 4,883,410); 3,4-dihydro-2,8-diisopropyl-3-oxo-2H-1,4-benzoxazine-4-acetic acid (U.S. Pat. No. 4,771,050); 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252, 572); N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060); (S)-6-fluorospiro[chroman-4,4'-imidazolidine]-2,5'-dione (sorbinil, U.S. Pat. No. 4,130, 714); d-2-methyl-6-fluoro-spiro(chroman-4',4'-imidazolidine)-2',5'-dione (U.S. Pat. No. 4,540,704); 2-fluoro-spiro (9H-fluorene-9,4'-imidazolidine)-2',5'-dione (U.S. Pat. No. 4,438,272); 2,7-di-fluoro-spiro(9H-fluorene-9,4'-imidazolidine)-2',5'-dione (U.S. Pat. No. 4,436,745, U.S. Pat. No. 4,438,272); 2,7-di-fluoro-5-methoxy-spiro(9H-fluorene-9,4'-imidazolidine)-2',5'-dione (U.S. Pat. No. 4,436,745, U.S. Pat. No. 4,438,272); 7-fluoro-spiro(5H-indenol[1,2-b]pyridine-5,3'-pyrrolidine)-2,5'-dione (U.S. Pat. No. 4,436,745, U.S. Pat. No. 4,438,272); d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357); spiro[imidazolidine-4,5'(6H)-quinoline]-2,5-dione-3'-chloro-7,'8'-dihydro-7'-methyl-(5'-cis) (U.S. Pat. No. 5,066,659); (2S,4S)-6- fluoro-2',5'-dioxospiro(chroman-4,4'-imidazolidine)-2-carboxamide (fidarestat, U.S. Pat. No. 5,447,946); and 2-[(4-bromo-2-fluorophenyl)methyl]-6-fluorospiro[isoquinoline-4(1H), 3'-pyrrolidine]-1,2',3,5'(2H)-tetrone (minalrestat, U.S. Pat. No. 5,037,831). Other compounds include those described in U.S. Pat. Nos. 6,720,348, 6,380,200, and 5,990,111, which are hereby incorporated by reference. Moreover, in other embodiments it is specifically contemplated that any of these may be excluded as part of the invention.

III. PHARMACEUTICAL COMPOSITIONS AND ROUTES OF ADMINISTRATION

Pharmaceutical compositions of the present invention may comprise an effective amount of one or more AR inhibitors dissolved or dispersed in a pharmaceutically acceptable carrier to a subject. The phrases "pharmaceutical" or "pharmacologically acceptable" refers to molecular entities and compositions that do not produce an adverse, allergic or other untoward reaction when administered to an animal, such as, for example, a human, as appropriate. The preparation of a pharmaceutical composition that contains at least one AR inhibitor or additional active ingredient will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

Pharmaceutically acceptable salts of the aldose reductase inhibitors of this invention may be readily prepared by reacting the free acid form of the aldose reductase inhibitor with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), and employing a solvent (e.g., ethyl acetate) from which the desired cationic salt precipitates, or can be otherwise isolated by concentration and/or addition of a non-solvent.

The acid addition salts of the aldose reductase inhibitors of this invention may be readily prepared by reacting the free base form of said aldose reductase inhibitor with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate, or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

In addition, the aldose reductase inhibitors that may be used in accordance with this invention, prodrugs thereof, and pharmaceutically acceptable salts thereof or of said prodrugs, may occur as hydrates or solvates. These hydrates and solvates are also within the scope of the invention.

A pharmaceutical composition of the present invention may comprise different types of carriers depending on whether it is to be administered in solid, liquid or aerosol form, and whether it needs to be sterile for such routes of administration as injection. A pharmaceutical composition of the present invention can be administered intravenously, intradermally, intraarterially, intraperitoneally, intraarticularly, intrapleurally, intrabronchially, intrapleurally, intranasally, topically, intramuscularly, intraperitoneally, subcutaneously, subconjunctival, intravesicularlly, mucosally, intrapericardially, intraumbilically, orally, topically, locally, inhalation (e.g., aerosol inhalation), instillation, injection, infusion, continuous infusion, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The number of doses and the period of time over which the dose may be given may vary. The practitioner responsible for administration will, in any event, determine the concentration of active ingredient(s) in a composition and appropriate dose(s), as well as the length of time for administration for the individual subject. An amount of an aldose reductase inhibitor that is effective for inhibiting aldose reductase activity is used. Typically, an effective dosage for the inhibitors is in the range of about 0.01 mg/kg/day to 100 mg/kg/day in single or divided doses, preferably 0.1 mg/kg/day to 20 mg/kg/day in single or divided doses. Doses of about, at least about, or at most about 0.01, 0.05, 0.1, 0.15, 0.20, 0.25, 0.30, 0.35, 0.40, 0.45, 0.50, 0.55, 0.60, 0.65, 0.70, 0.75, 0.80, 0.85, 0.90. 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg/day, or any range derivable therein. Typically the dose will be 25 to 1200 mg per day and in certain aspects is between 100 and 800 mg per day.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In certain aspects of the invention, the AR inhibitors are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle containing the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In particular embodiments, prolonged absorption of an injectable composition can be brought about by the use in the compositions of agents delaying absorption, such as, for example, aluminum monostearate, gelatin or combinations thereof.

In order to increase the effectiveness of treatments with the compositions of the present invention, such as an AR inhibitor, it may be desirable to combine it with other therapeutic agents. This process may involve contacting the cell(s) with an AR inhibitor and a therapeutic agent at the same time or within a period of time wherein separate administration of the modulator and an agent to a cell, tissue or organism produces a desired therapeutic benefit. The terms "contacted" and "exposed," when applied to a cell, tissue or organism, are used herein to describe the process by which a AR inhibitor and/or therapeutic agent are delivered to a target cell, tissue or organism or are placed in direct juxtaposition with the target cell, tissue or organism. The cell, tissue or organism may be contacted (e.g., by administration) with a single composition or pharmacological formulation that includes both a AR inhibitor and one or more agents, or by contacting the cell with two or more distinct compositions or formulations, wherein one composition includes an AR inhibitor and the other includes one or more agents.

The AR inhibitor may precede, be concurrent with and/or follow the other agent(s) by intervals ranging from minutes to weeks. In embodiments where the AR inhibitor and other agent(s) are applied separately to a cell, tissue or organism, one would generally ensure that a significant period of time did not expire between the time of each delivery, such that the inhibitor and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the modulator. In other aspects, one or more agents may be administered within of from substantially simultaneously, about 1 minute, about 5 minutes, about 10 minutes, about 20 minutes about 30 minutes, about 45 minutes, about 60 minutes, about 2 hours, or more hours, or about 1 day or more days, or about 4 weeks or more weeks, or about 3 months or more months, or about one or more years, and any range derivable therein, prior to and/or after administering the AR inhibitor.

In such combinations, AR inhibitors and other active agents may be administered together or separately. In addition, the administration of one agent may be prior to, concurrent to, or subsequent to the administration of other agent(s).

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Cigarette Smoke Extract

1. Results

CSE caused a dose-dependent cell-death in SAEC that was 23, 26, 37 and 40% in 24 h at 12.5, 25, 50 and 75% concentration of CSE, respectively. The treatment of SAEC with fidarestat prevented CSE-induced cell death such that at 50% CSE>85% cells were alive and at 12.5% more than 95% cells were alive (FIG. 1). TNF-α-induced cell death in SAEC was used as a positive control.

Figure 2:
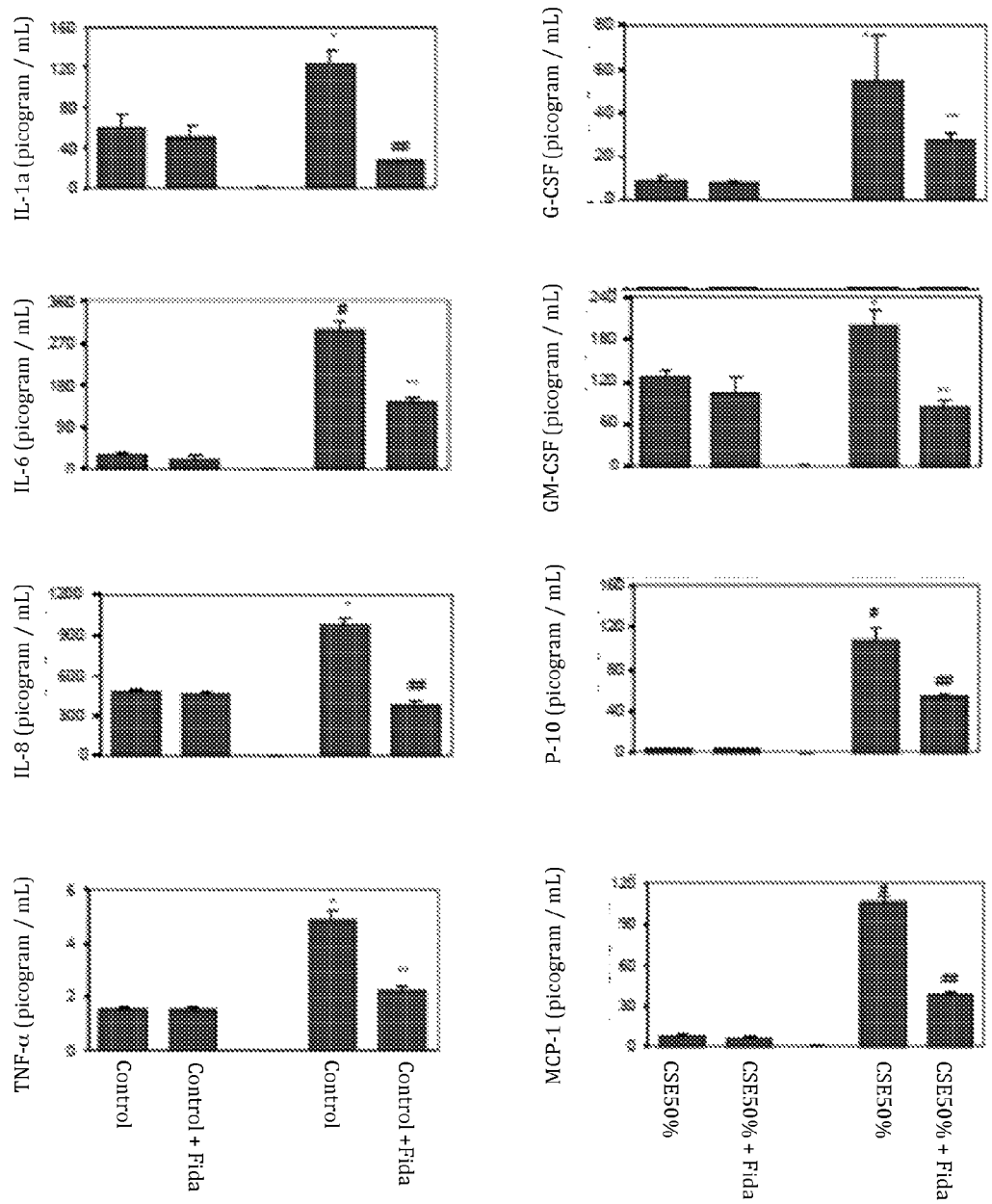
FIG. 2. CSE-induced changes in cytokine levels in SAEC prevented by aldose reductase (AR) inhibition. $*p<0.01$ Vs Control; $**p<0.05$ Vs CSE 50%; $\#p<0.001$ Vs Control; $\#\#p<0.01$ Vs CSE 50%

Further, levels of cytokines, chemokines and growth factors were measured in the SAEC culture media after 24 h of CSE (50%) treatment (FIG. 2). The levels of cytokines such as IL-1a and IL-8 increased by approximately 2-folds where as that of by approximately 10-folds and TNF-α by 3-folds. All the changes were significantly ($p<0.05$ and 0.01) prevented by AR inhibition in SAEC (FIG. 2). Similarly, there was significant increase in the levels of chemokines such as G-CSF (~7-folds), MCP-1 (~15 folds), GM-CSF (~0.75 fold) and IP-10 (more than 30-folds) and growth factors such as TGF-α(3-folds) and VEGF (4-folds) and treatment with AR inhibitor prevented these changes by more than 50% (FIG. 2).

2. Materials and Methods

Selection of the Cells:

The airway epithelial cells, which are the point of first contact between the allergens and the respiratory system, plays an important function as a barrier to foreign particles including environmental gases and particles, cigarette smokes and other xenobiotics which disturb cellular redox homeostasis leading to changes in cell viability, morphology and physiology of airway epithelial cells resulting in COPD. Therefore we chose primary human small airway epithelial cells.

Cell Culture:

Primary human Small Airway Epithelial Cells (SAEC) obtained from Lonza (Walkersville, Md.) were normal human SAEC harvested from distal airspace of 18 yrs old male donor. The cells were cultured according to the supplier's instructions at 37° C. in humidified atmosphere containing 95% air and 5% $CO_2$ in small airway epithelial basal medium (SABM) with supplements containing 52 µg/ml bovine pituitary extract, 0.5 ng/ml human recombinant epidermal growth factor (EGF), 0.5 µg/ml epinephrine, 1 µg/ml hydrocortisone, 10 µg/ml transferrin, 5 µg/ml insulin, 0.1 ng/ml retinoic acid (RA), 6.5 ng/ml triiodothyronine, 50 µg/ml Gentamicin/Amphotericin-B (GA-1000), and 50 µg/ml fatty acid-free bovine serum albumin (BSA).

Preparation of Cigarette Smoke Extract (CSE):

Research-grade cigarettes (1R3F) with a filter from the Kentucky Tobacco Research and Development Center at the University of Kentucky (Lexington, Ky.) were smoked to 0.5 cm above the filter in a fume hood, using a modification of the method developed by Carp and Janoff (*Am Rev Respir Dis.* 1978; 118(3):617-621). CSE was prepared by bubbling smoke from 1 cigarette into 10 ml of serum-free media at a rate of 1 cm/min and labeled as 100%. Various concentrations of CSE were prepared by diluting with media. The pH of the media was adjusted to 7.4 and the medium was sterile filtered with a 0.2-µm filter (Millipore). The CSE was always prepared fresh on the day of the experiment.

Cell Viability Assays:

The SAEC were plated at the density of 5000 cells/well in a 96-well plate and growth-arrested for 24 h by replacing complete medium with fresh basal medium containing fidarestat (20 µM) or carrier. The cells were incubated with CSE (75, 50, 25, 12.5, 0%) for an additional 24 h with or without fidarestat, after which 10 µl of MTT (5 mg/ml) was added to each well and incubated at 37° C. for an additional 2 h. The medium was removed and the formazan granules were dissolved in 100% DMSO. Absorbance was read at 570 nm using a 96-well ELISA plate reader.

Determinations of Cytokines and Chemokiens by Milliplex in Cell Culture Media:

Cells were grown to confluence and washed with PBS before CSE or vehicle exposure. To mimic smoking of one cigarette, the cells were exposed to CSE for 15 min. The CSE was removed; the cells were washed with PBS and placed in fresh medium. The culture media were collected cleared by centrifugation at 2,500 rpm for 5 min. The supernatant was stored at –200° C. until used for analysis. The levels of cytokines and chemokines in the supernatant were determined by Milliplex MAP kits according to the manufacturer's instructions (Millipore Corporation, Bellerica, Mass.)).

Statistics:

Data presented as mean±SD and statistical significance was determined by unpaired Student's t test using graph pad prism software (GraphPad Software, Inc. La Jolla, Calif.). The value of $P<0.05$ was considered as statistically significant.

B. Ragweed Pollen Extract

Stimulation with Ragweed pollens, allergens, growth factors, or cytokines cause increased ROS production inside the cells. The ROS could oxidize membrane lipids to form lipid aldehydes such as 4-hydroxynonenal (HNE), which readily reacts with glutathione and form GS-conjugates such as GS-HNE. AR catalyzes the reduction of GS-HNE into GS-1,4-dihydroxynonene (GS-DHN). The latter is known to activate various downstream protein kinases such as PKC, PI3K and MAPK activating transcription factors NF-κB and AP-1, which transcribes various inflammatory markers, including IL-13, which in paracrine fashion induces more ROS formation. The GS-DHN could also phosphorylate JAK-1 and MAPK such as ERK1/2, eventually phosphorylating and activating STAT-6, which translocate to the nucleus and transcribe genes including mucin genes—leading to goblet cell metaplasia. The continuously formed GS-DHN may amplify the signaling loop by increased ROS production via PKC/NOX pathway. Inhibition of AR blocks the initial as well as the amplification loop and prevents ROS-induced pathological changes (Ramana et al. *J Biol Chem* 281: 33019-33029, 2006; Tammali et al. Cancer Res 66: 9705-9713, 2006).

1. Results

Figures 3A, 3B:
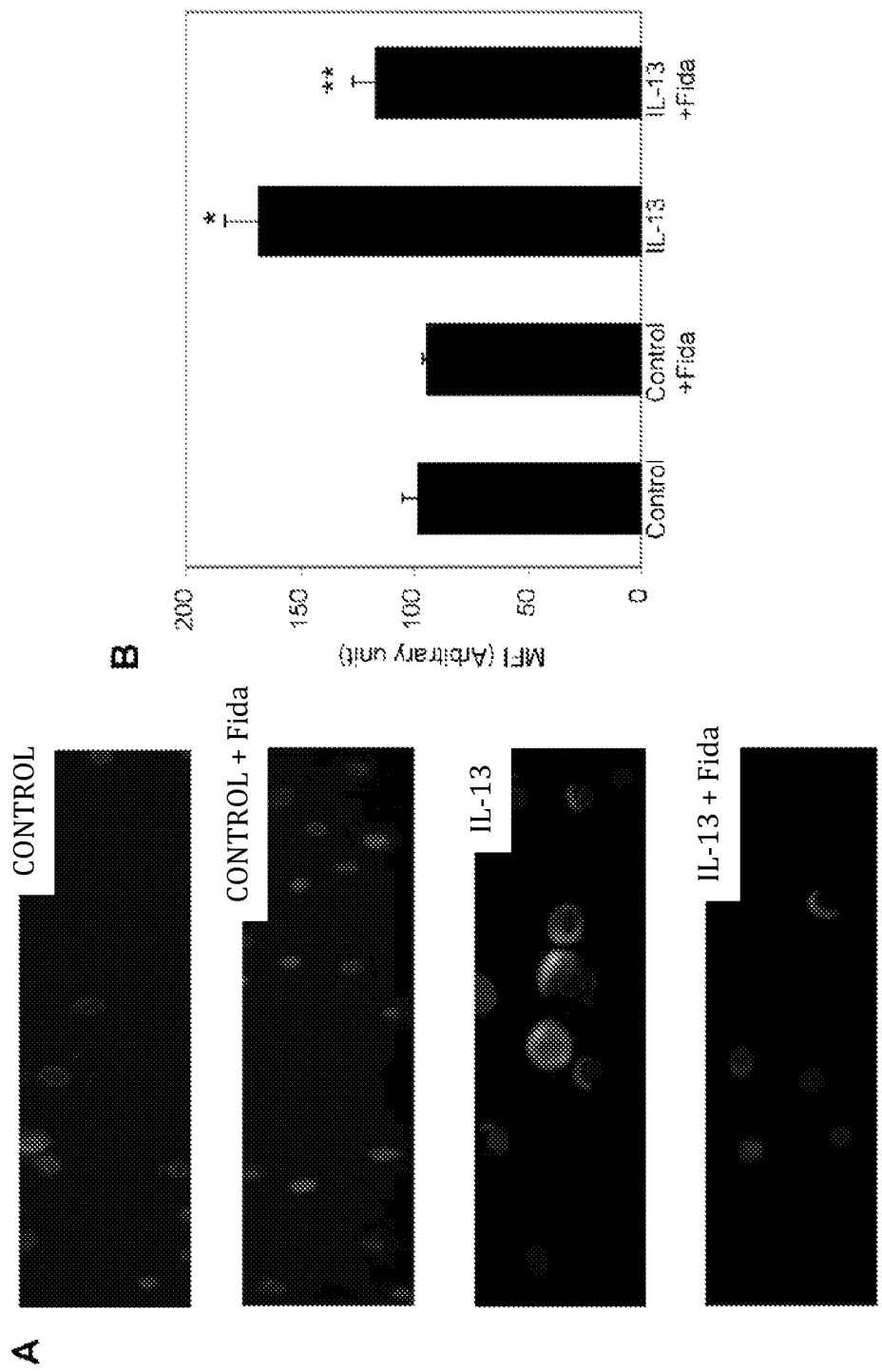
FIGS. 3A-3B. Inhibition of AR prevents IL-13-induced reactive oxygen species (ROS) production in SAEC. (A) Approximately $5\times10^4$ cells were seeded on 2-chambered slides and starved in serum-free basal medium without or with fidarestat overnight. The cells were washed with 1×HBSS and incubated with 10 µM H2DCF-DA at 37° C. for 30 min, washed again and treated with IL-13 (25 ng/ml) for 1 h. The cells were washed with cold 1×HBSS twice and mounted using floursave mounting medium with DAPI. Photomicrographs were acquired using a fluorescence microscope (Nikon). A representative image is shown (n=4); Magnification 400×. (B) Approximately 10,000 SAEC were plated per well in a 96-well plate and serum-starved for 24 h without or with fidarestat. The cells were washed with 1×HBSS and incubated with 10 µM H2DCF-DA at 37° C. for 30 min. Cells were washed again to remove excess H2DCF-DA and treated with 11-13 (25 ng/ml) in basal media for 1 h. At the end of the treatment, cells were washed twice with HBSS and fluorescence was determined at 485 nm excitation and 538 nm emission wavelengths. Relative ROS production is expressed as mean fluorescence intensity (MFI) (arbitrary units). The bars represent mean±SD (n=4-6); ($*p<0.01$ vs. Control; $**p<0.05$ vs. IL-13).

AR Inhibition Prevents IL-13-Induced ROS Levels in SAEC:

Since cytokines-induced oxidative stress is known to mediate molecular signaling that leads to differentiation of airway epithelial cells into mucus cells, so we determined the effects of AR inhibition on IL-13-induced ROS levels in SAEC by two different methods. As shown in FIGS. 3A and 3B, stimulation with IL-13 caused approximately twofold increase in the ROS levels over the control and treatment of the cells with fidarestat significantly (80%) prevented the increase. These results suggest that cytokine-induced oxidative stress could be prevented by inhibition of AR.

Figures 4A, 4B:
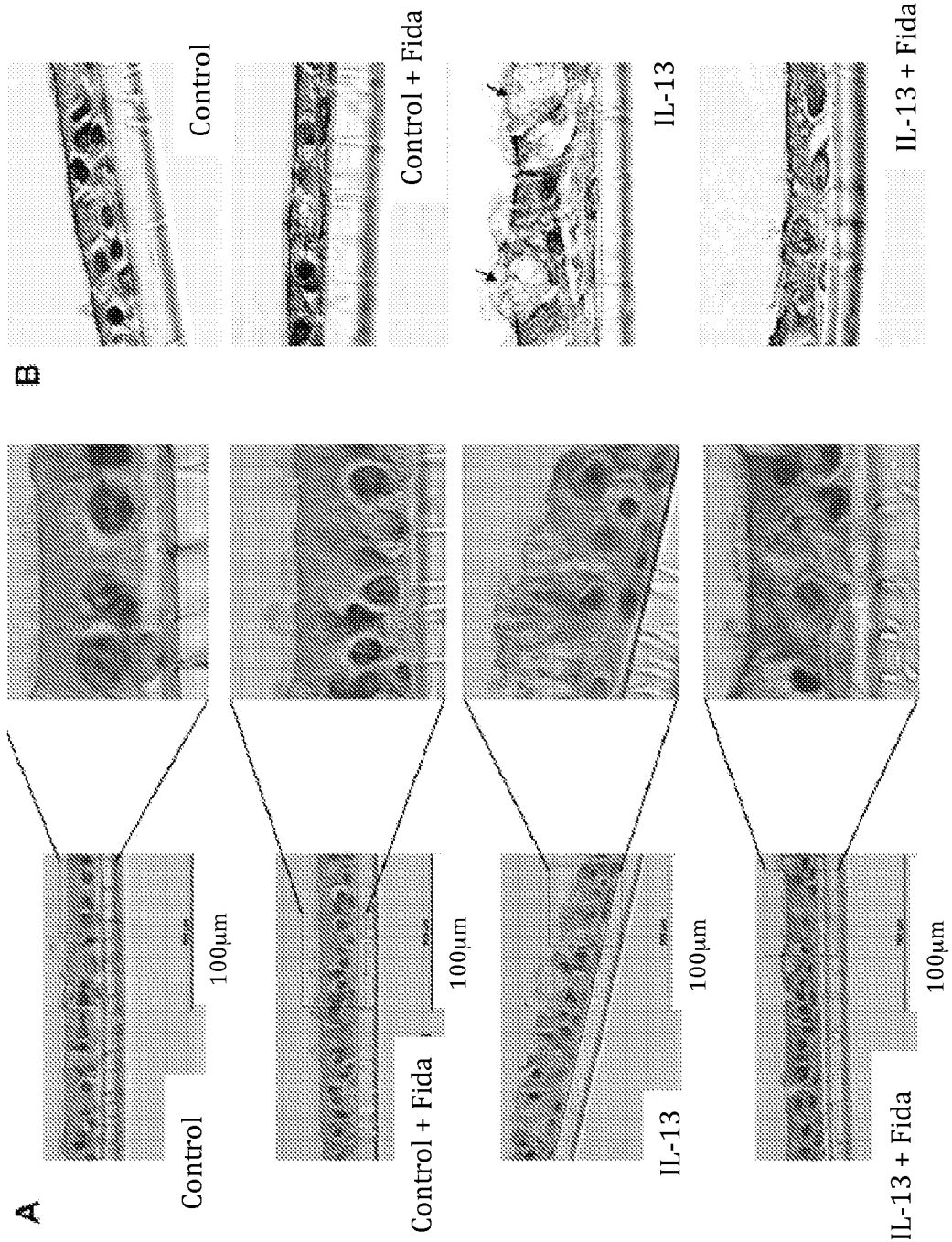
FIGS. 4A-4B. AR inhibition prevents IL-13-induced loss of cilia and β-tubulin in airway epithelial cell monolayer. Approximately $8.5\times10^4$ SAEC were seeded per 12 mm diameter PET transparent insert and cultured for 7 days in differentiation media supplied from both lower and upper sides followed by culture on ALI for 11 days for differentiation into ciliated cells. The monolayer was treated with AR inhibitor for overnight and stimulated with IL-13 for 48 h. The monolayers on the membrane inserts were fixed for 24 h in z-fix (10% buffered formalin with zinc) at 4° C., paraffin embedded and 5 µM sections were cut. (A) The H&E stained sections were examined under the light microscope; magnification 400×. Inset shows magnified view of the selected regions from each representative photomicrograph (n=4). (B) Immunohistochemistry using β-tubulin antibodies was performed on the sections. Dark brown staining in the monolayer corresponds to cilia axoneme β-tubulin. Arrows show loss of β-tubulin as the ciliated cells transform into goblet cells. A representative photomicrograph has been shown (n=4); magnification 400×.

AR Inhibition Prevents IL-13-Induced Goblet Cell Metaplasia in SAEC:

To investigate the role of AR in the regulation of goblet cells metaplasia and mucin production, the inventors used an air-liquid interface culture system that mimics in-vivo airway environment. First, the inventors cultured primary human airway epithelial cells on polyethylene terephthalate (PET) membrane insert with collagen type-1 coating. The cells on the collagen-coated membrane insert formed a consistent 2-3 cells thick layer of airway cells. Further, the monolayer cells fully differentiated into ciliated cells when cultured on the ALI in EGF-containing medium for 11 days (FIG. 4A) and when these cells were stimulated with IL-13 for 48 h, the number of ciliated cells were markedly reduced as also determined by immunostaining using β-tubulin specific antibodies. However, AR inhibition by fidarestat preserved the ciliated morphology (FIG. 4B). AR inhibitor alone had no toxic effects and the monolayers of ciliated cells were largely intact. As determined by PAS staining a large number of ciliated cells (~6-fold) transformed into mucus-laden goblet cells when stimulated with IL-13 for 48 h, whereas addition of AR inhibitor, fidarestat, in the medium prior to IL-13 challenge prevented the airway cells from differentiating into goblet cells (data not shown).

Figures 5A, 5B, 5C:
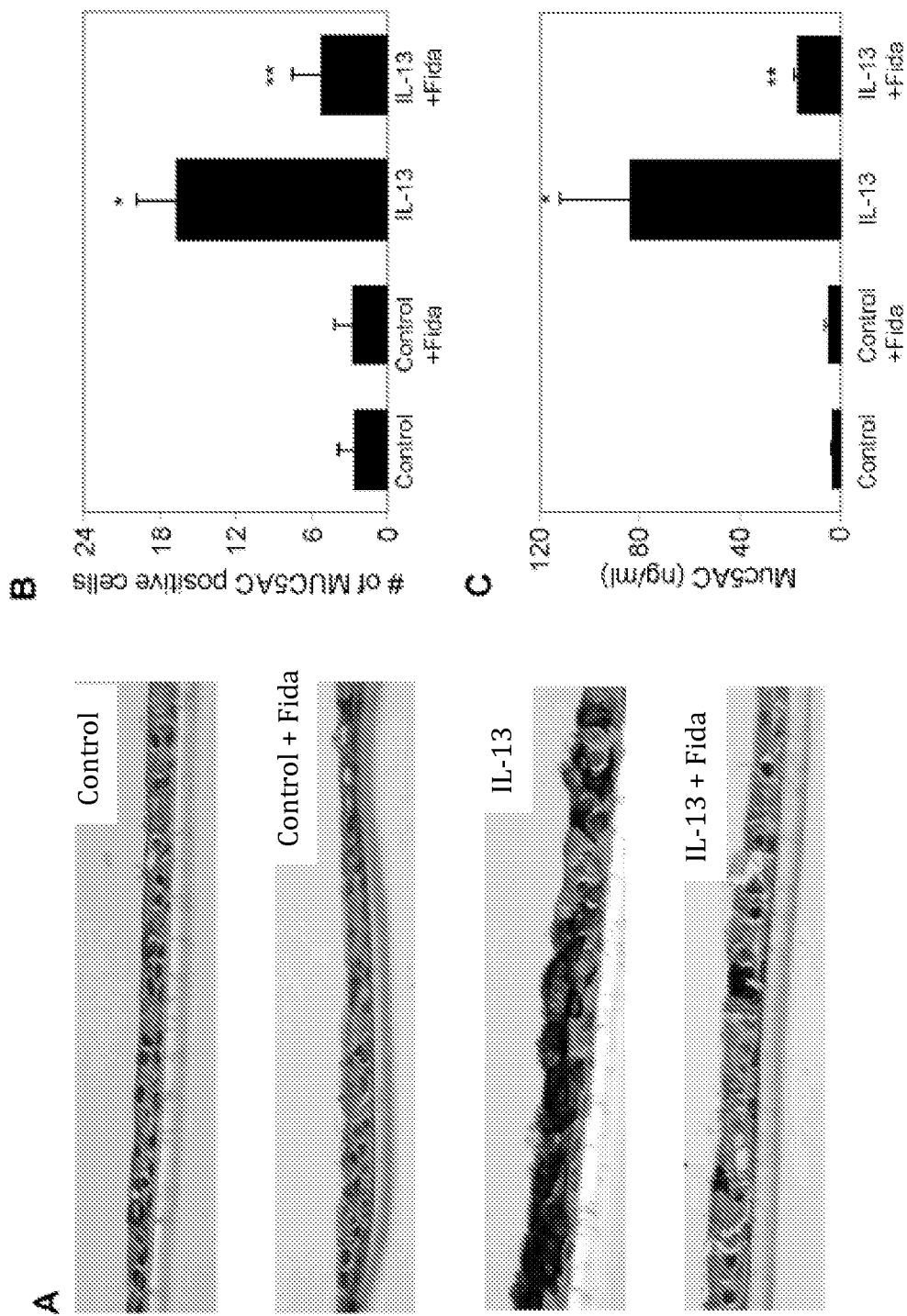
FIGS. 5A-5B. AR inhibition prevents IL-13-induced goblet cell metaplasia and expression of Muc5AC in airway epithelial monolayer. (A) The well-differentiated airway epithelial cells at air-liquid interface (ALI) were incubated with IL-13 for 48 h without or with AR inhibitor, fidarestat. The monolayer was fixed as described and immunohistochemistry using Muc5AC antibodies was performed on the sections. A representative photomicrograph is shown (n=4); magnification 400×. (B) The bar diagram shows number of Muc5AC positive cells per viewing area from 10 areas counted randomly from each section under the microscope (n=4); $*p<0.0005$ vs Control; $**p<0.004$ vs IL-13. (C) The airway epithelial monolayer was incubated with IL-13 submerged in basal medium for 48 h in the absence and presence of AR inhibitor, fidarestat. The culture medium was collected from the top chamber and utilized for determination of Muc5AC by an ELISA, (n=4); $*p<0.005$ vs Control; $**p<0.01$ vs IL-13.

AR Inhibition Prevents IL-13-Induced Expression of Mucin and SPDEF in Airway Epithelial Monolayer:

Next, sections of monolayer cells were stained with antibodies against Muc5AC. As shown in FIGS. 5A and 5B, IL-13 stimulation resulted in a large number of Muc5AC immuno-positive cells. When the cells were treated with AR inhibitor and incubated with IL-13, the number of cells with Muc5AC positive staining decreased significantly (~70%) suggesting that only a few cells had transformed into goblet cells. Next, the inventors measured the level of secreted Muc5AC in the culture medium using an ELISA. There was a marked increase in the secretion of Muc5AC in the medium after IL-13 stimulation that was significantly (~80%) prevented by treatment with AR inhibitor (FIG. 5C). These results suggest that AR regulates IL-13-mediated metaplasia and mucus production in the airway epithelial cells and inhibition of AR could prevent these events.

Figures 6A, 6B:
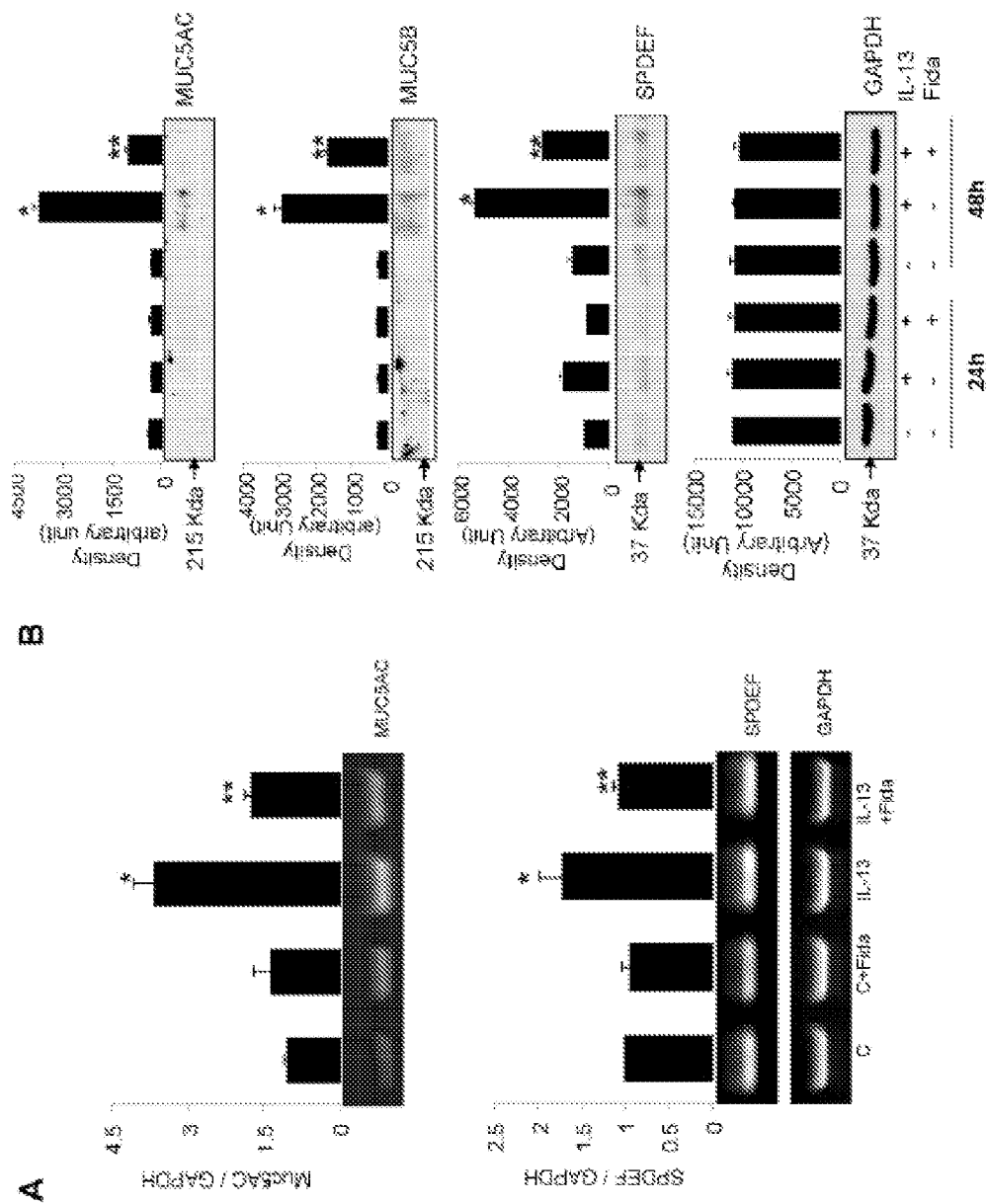
FIGS. 6A-6B. AR inhibition prevents IL-13-induced expression of Mucin and transcription factor SPDEF in airway epithelial cell monolayer. (A) The airway epithelial cell monolayer at ALI was serum starved without or with fidarestat and incubated with IL-13 for 18 h. Total RNA was isolated and subsequently RT-PCR was performed to assess the expression of Muc5AC and SPDEF. The bar diagrams show densitometric analysis of the corresponding blots (n=4). $*p<0.001$ vs Control; $**p<0.001$ vs IL-13; (B) The monolayer of ciliated airway cells at ALI was treated with AR inhibitor for 24 h and subsequently incubated with IL-13 for 24 or 48 h. At the end of incubation, cell lysate was prepared and subjected to western blotting using antibodies against Muc5AC, Muc5B, and SPDEF. The membranes were stripped and re-probed with antibodies against GAPDH to show the equal loading of protein. A representative blot is shown (n=4). $*p<0.0001$ vs Control; $**p<0.001$ vs IL-13.

Next, the inventors examined whether Mucin levels in these cells were regulated by transcription or translation. As shown in FIG. 6A, upper panel, Muc5AC-specific RNA expression increased by approximately 3-fold in IL-13-treated SAEC monolayer and fidarestat significantly prevented the increase. A number of studies have shown that SPDEF regulates the expression of several genes in the airway epithelial cells including both acidic and neutral mucins and cause goblet cell hyperplasia. The inventors therefore, determined the expression of SPDEF mRNA levels by RT-PCR in our cell-culture model and observed that IL-13 significantly enhanced the expression of SPDEF in epithelial cells, whereas control cells had only basal level of expression. When these cells were treated with AR inhibitor prior to IL-13 stimulus, the SPDEF mRNA levels decreased significantly (FIG. 6A, lower panel).

Next the levels of Muc5AC and Muc5B proteins were measured by immunoblotting in SAEC monolayer after incubation with IL-13 for 24 and 48 h. Muc5AC/B were not detectable after 24 h however, after 48 h of incubation with IL-13 there was a robust increase in the expression of protein levels (FIG. 6B, top two panels), which was significantly (~75 and ~50%, respectively) prevented in fidarestat treated cells. Also in the airway epithelial cell monolayer incubated with IL-13, the levels of SPDEF protein in the cells significantly increased after 24 h and further increased after 48 h and the increase was significantly (~50%) prevented by AR inhibitor treated cells (FIG. 6B). The decrease in the levels of protein corresponded with the decrease in mRNA levels of SPDEF and Muc5AC/B suggesting that SPDEF and Muc5AC genes are induced in the presence of IL-13, and that the expression of Muc5AC is prevented by AR inhibition at the level of transcription.

Figure 7:
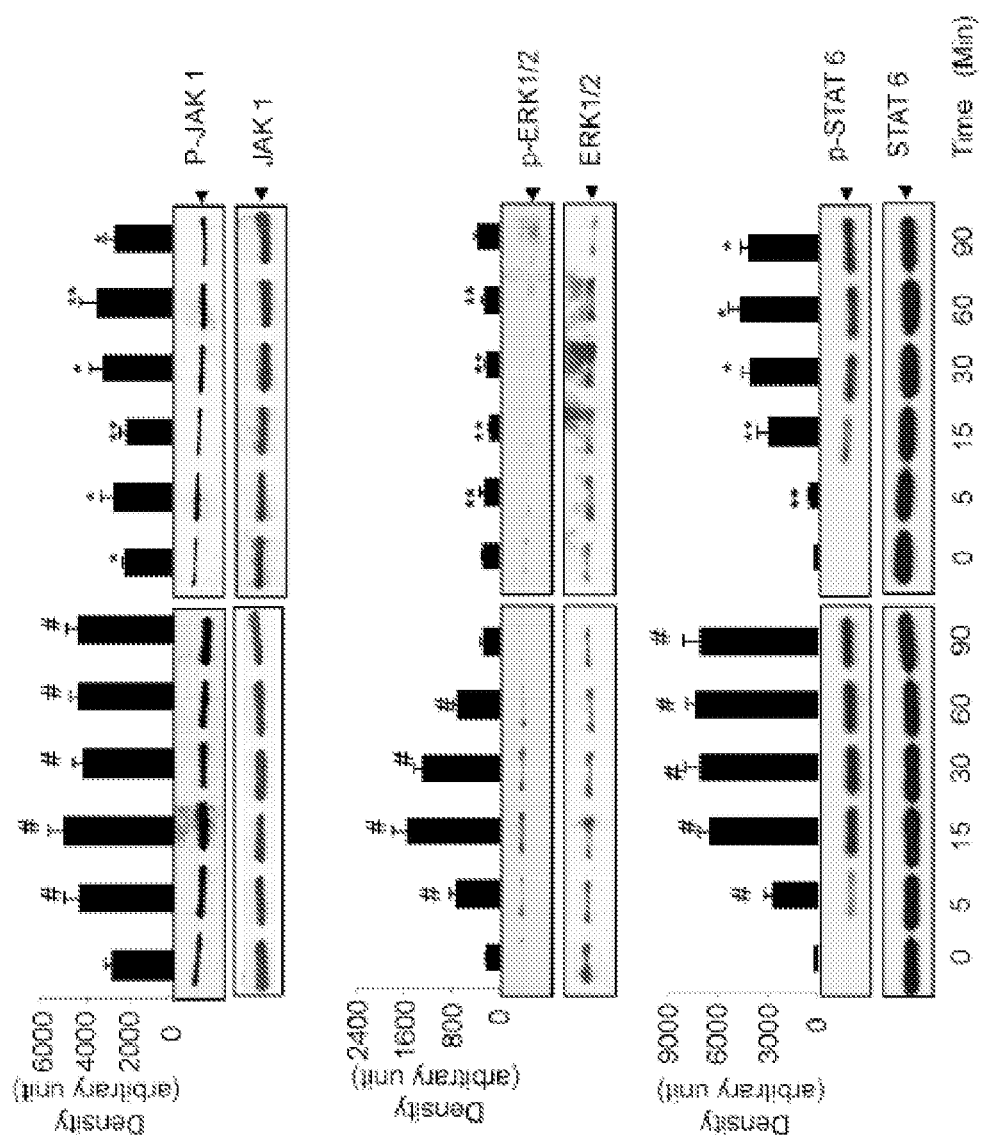
FIG. 7. AR inhibition prevents IL-13-induced phosphorylation of JAK-1, ERK1/2 and STAT-6 in airway epithelial monolayer. The ciliated monolayer of airway cells at ALI was treated with AR inhibitor for 24 h and stimulated with IL-13 for different time periods as indicated. At the end of incubation, cells were lysed and cell lysate was subjected to western blotting using antibodies against phosphorylated and non-phosphorylated JAK-1, ERK1/2 and STAT-6 to analyze the activation of these signaling proteins. A representative blot is shown (n=4). #p<0.001 vs Control; *p<0.01 and **p<0.001 vs IL-13.

AR Inhibition Prevents IL-13-Induced Phosphorylation and Activation of Signaling Intermediates:

Since AR inhibition in airway epithelial cells monolayer on ALI successfully prevented the expression of transcription regulator SPDEF and subsequent expression of mucin, the effect of AR inhibition on the molecular mechanism(s) that regulates the expression of these mediators of asthma was studied. Cells grown on ALI were stimulated with IL-13 in presence or absence AR inhibitor and determined the phosphorylation of JAK1, ERK1/2 and STAT-6 proteins. As shown in FIG. 7, IL-13 caused a time-dependent increase in the phosphorylation of STAT-6 and upstream mediators such as JAK1 and ERK1/2. When these cells were treated with AR inhibitor prior to IL-13 stimulus, the phosphorylation of these proteins decreased significantly. Further, in cells treated with AR inhibitor alone the basal phosphorylation of JAK1 but not ERK1/2 and STAT-6 was decreased. These results suggest that AR regulates the activation of key signaling intermediates involved in goblet cell metaplasia that transforms airway-ciliated epithelial cells to mucus secreting goblet cells.

Figure 8:
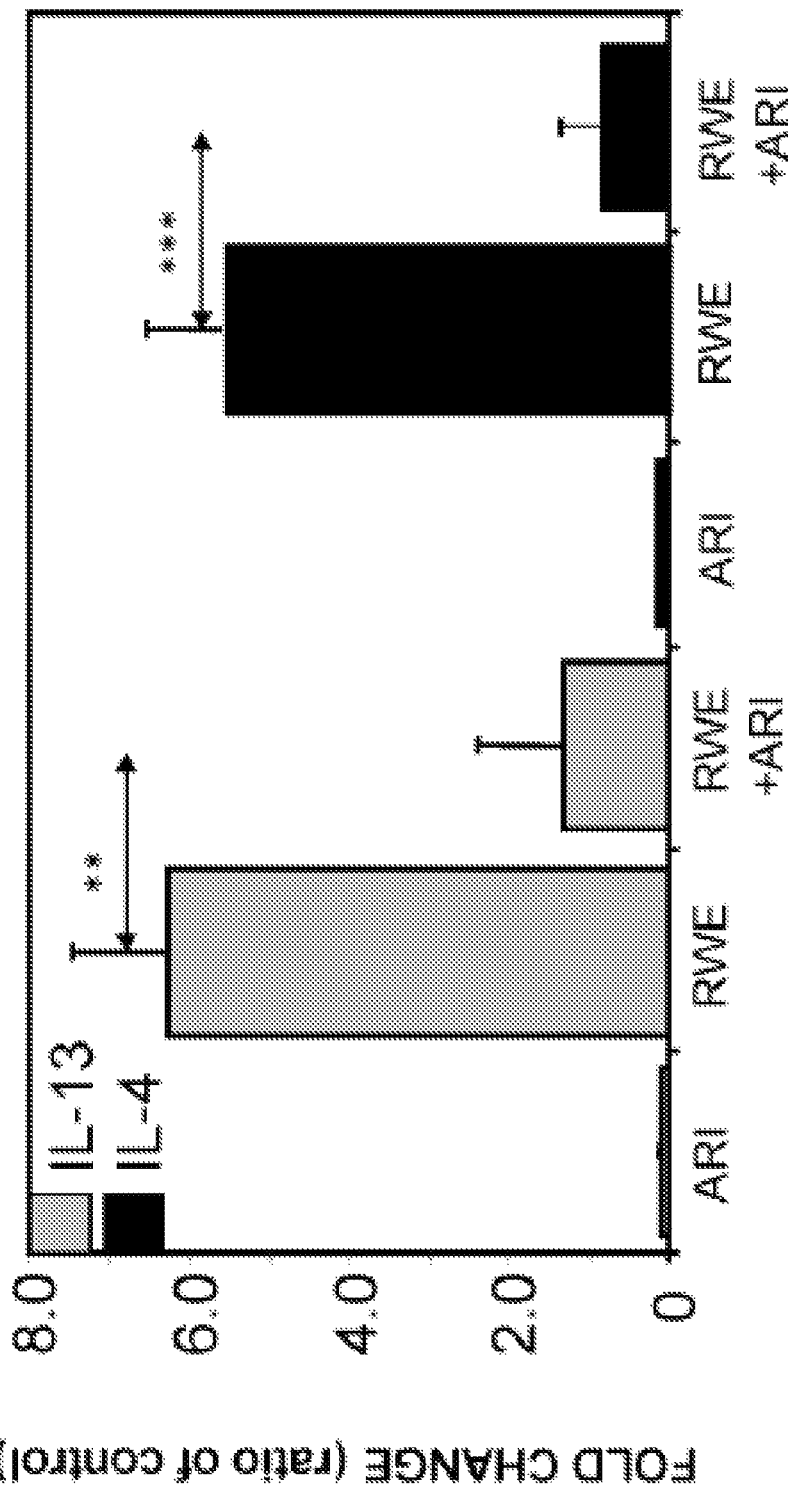
FIG. 8. AR inhibition prevents RWE-induced expression of IL-13 in mouse lung. The mice were sensitized and challenged with PBS or RWE, without or with AR inhibitor and 16 h later lungs were harvested and total RNA was isolated (n=4). One microgram of total RNA from each sample was transcribed into first-strand cDNA and quantitative RT-PCR was conducted using IL-13 specific forward and reverse primers. The levels of RNA for the target sequences were determined by melting curve analysis. The values presented here are fold-change over the control. (**p<0.001). RWE, ragweed pollen extract; ARI, aldose reductase inhibitor.
Figures 9A, 9B:
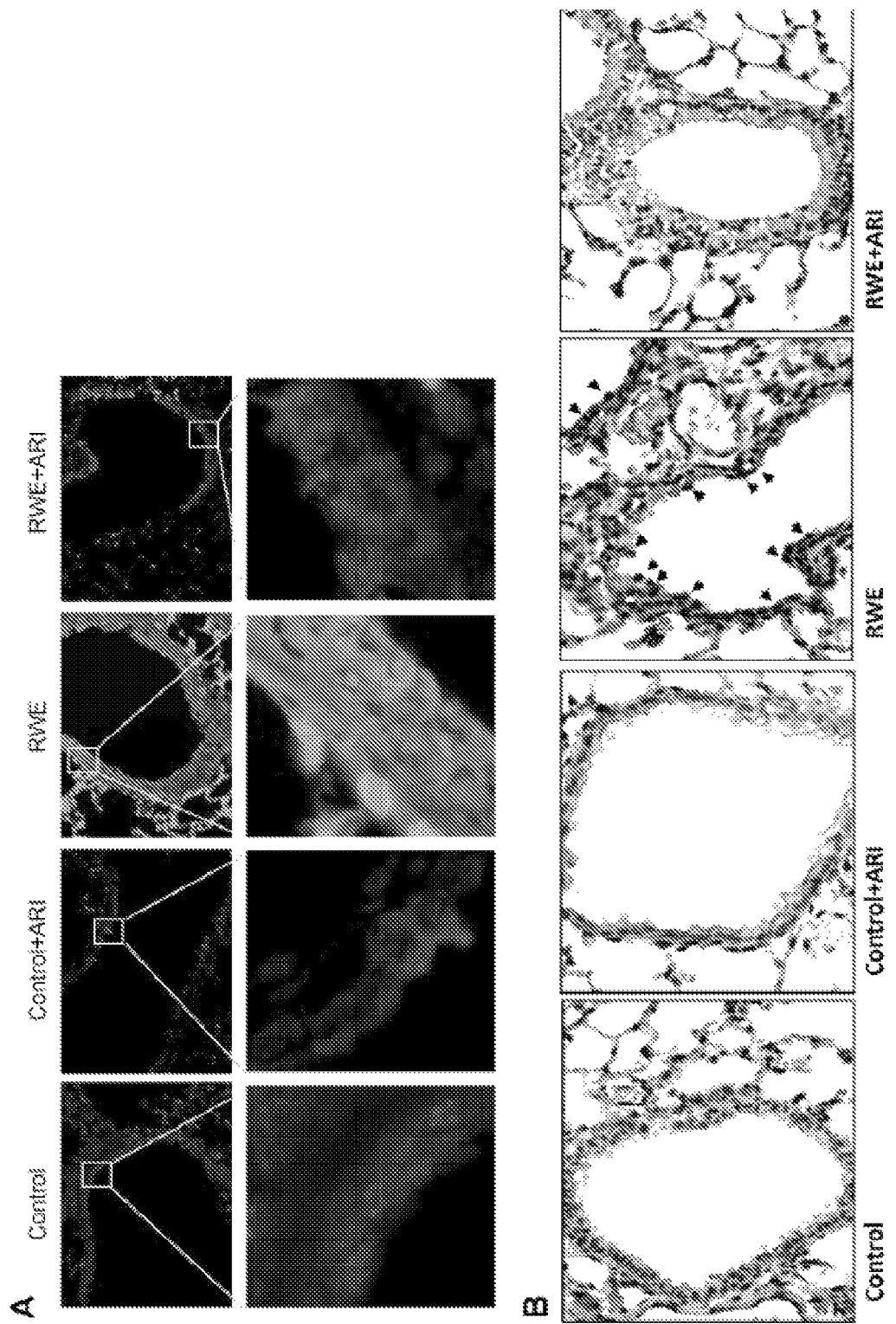
FIGS. 9A-9B. AR inhibition prevents phosphorylation of STAT-6 in mouse lung epithelium. The mice were sensitized and challenged with PBS or RWE, without or with AR inhibitor and 20 h later lungs were perfused and fixed with 4% paraformaldehyde, embedded in paraffin, and sectioned to 5 μM. The sections were immunostained with p-STAT-6 specific antibodies using immunofluoroscence secondary antibodies (A) or DAB-based HRP conjugated antibodies counterstained with hematoxylin and eosin (B). Photomicrographs were acquired by fluorescence or light microscopy. A representative field for each group is shown (magnification: 200×). In (A) inset shows magnified view of the selected regions from representative photomicrographs (n=4). RWE, ragweed pollen extract; ARI, aldose reductase inhibitor.

AR Inhibition Prevents RWE-Induced Expression of IL-13 and Activation of STAT-6 in Mouse Lung:

Since Th2 cytokines, especially IL-13, is involved in the goblet cell metaplasia, the inventors examined the expression levels of IL-13 in mice lung after RWE challenge and found that its level increased approximately 6-fold compared to control and treatment with fidarestat prior to challenge prevented this increase (FIG. 8). To examine whether increased IL-13 levels coincided with the phosphorylation and activation of STAT-6, which play a major role in metaplasia, the mice were killed after 20 h of RWE challenge and performed immunofluorescence studies on the lung section using phospho-STAT-6 antibodies. It was observed that while the lungs of control mice showed only background, RWE-challenged mice lung epithelium showed a marked increased in the fluorescence intensity specific to phospho-STAT-6, which was prevented by AR inhibition (FIG. 9A). The results were confirmed by DAB-based immunohistochemistry on the lung sections as well (FIG. 9B). These results suggest that inhibition of AR could prevent the allergen-induced IL-13 expression and subsequent activation of STAT-6 in vivo.

Figures 10A, 10B:
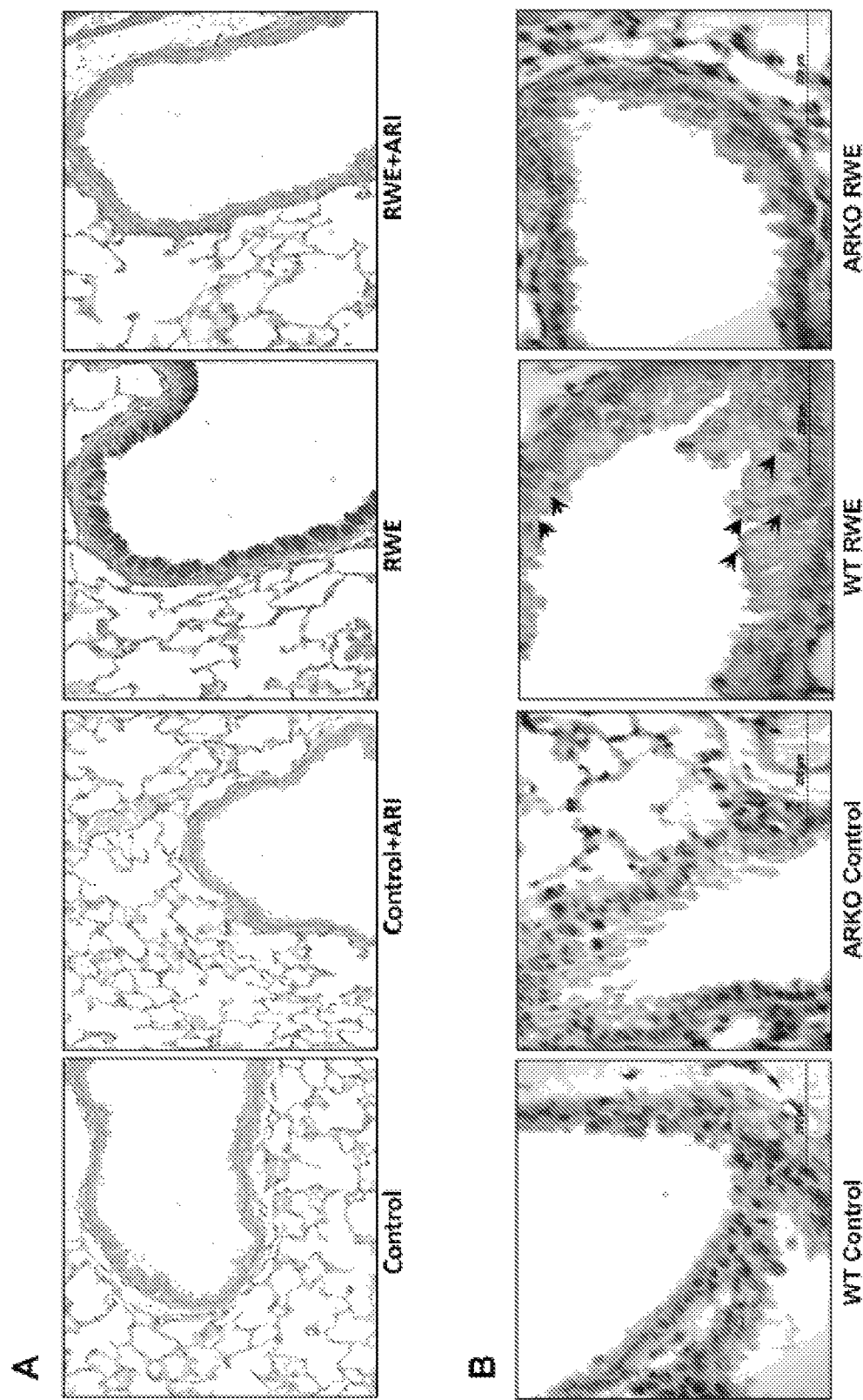
FIGS. 10A-10B. Inhibition or deficiency of AR prevents RWE-induced goblet cell metaplasia in mice lungs. RWE-sensitized normal and AR-null mice were challenged with RWE and 72 h later the lungs were harvested from mice treated without or with AR inhibitor (A) or AR-null mice (B), perfused and fixed with 4% paraformaldehyde and embedded in paraffin. The sections were stained with PAS stain and observed under light microscope and photomicrographs were acquired. A representative photomicrograph from each group is shown (n=4). Magnification 200× (A); 400× (B).

AR Inhibition/Deficiency Prevents RWE-Induced Goblet Cell Metaplasia in Mice Lung:

The inventors next examined the effect of AR inhibition on goblet cell metaplasia in RWE-sensitized and -challenged mice. After 72 h of challenge the lung sections were obtained and stained with PAS and changes in the airway epithelia were examined. As shown in FIG. 10A, there was a significant increase in the PAS positive cells in the airway of RWE-challenged mice and absent in the lungs of mice treated with fidarestat prior to RWE challenge. Similar to the inhibitor-treated mice, AR-null mice challenged with RWE showed absence of PAS positive cell in the airway (FIG. 10B). These results further confirm that AR plays a significant role in the goblet cell metaplasia and AR inhibition could prevent metaplasia in allergic asthma.

2. Materials and Methods

Animals:

All animal experiments were performed according to the National Institutes of Health Guide for Care and Use of Experimental Animals and approved by University of Texas Medical Branch Animal Care and Use Committee (Animal welfare assurance No. A3314-01).

Reagents:

Small airway epithelial basal medium (SABM), and small airway epithelial growth media (SAGM™) bulletkit; and Reagentpack™ containing Trypsin 0.025%/EDTA 0.01%, Trypsin neutralizing solution and HEPES buffered-saline solution were purchased from Lonza Walkersvillle Inc. (Walkersville, Md.). Dulbecco's modified Eagle's medium (DMEM) and phosphate buffered saline (PBS) were purchased from Gibco, Invitrogen (Grand Island, N.Y.). AR inhibitor, fidarestat, was a gift from Sanwa-Kayagu (South Korea). Human recombinant IL-13 was from R & D systems (Minneapolis, Minn.). Dimethyl sulfoxide (DMSO) was obtained from Fischer scientific (Pittsburg, Pa.). Human mucin5AC ELISA kit was from Cosmo Bio USA (Carlsbad, Calif.). Antibodies against STAT-6, phospho-STAT-6, phospho-JAK1, JAK1, ERK1/2, phospho-ERK1/2 were from Cell Signaling Tech (Danvers, Mass.) and mucin 5 subtypes A and C (Muc5AC), Muc5B, GAPDH and β-actin antibodies were from Santa Cruz Biotechnology Inc. (Santa Cruz, Calif.). Antibodies against SAM pointed domain-containing ETS transcription factor (SPDEF) were purchased from Abcam Inc. (Cambridge Mass.). The polyethylene pteraphthalate transparent 12-well Millicell cell culture insert with 1.0 μM pores were purchased from Millipore Corp. (Billerica, Mass.). Rat tail collagen type 1 and all trans-retinoic acid were from Sigma-Aldrich (Saint Louis, Mo.). The reagents used in the Western blot analysis were obtained from Sigma. All other reagents used were of analytical grade.

Cell Culture:

Primary human Small Airway Epithelial Cells (SAEC) obtained from Lonza Walkersville, Inc. (Walkersville, Md.) were normal human SAEC harvested from distal airspace. The cells were cultured and maintained according to the supplier's instructions at 37° C. in humidified atmosphere containing 95% air and 5% $CO_2$ in small airway epithelial basal medium (SABM) supplemented with 52 μg/ml bovine pituitary extract, 0.5 ng/ml human recombinant epidermal growth factor (EGF), 0.5 μg/ml epinephrine, 1 μg/ml hydrocortisone, 10 μg/ml transferrin, 5 μg/ml insulin, 0.1 ng/ml retinoic acid (RA), 6.5 ng/ml triiodothyronine, 50 μg/ml Gentamicin/Amphotericin-B (GA-1000), and 50 μg/ml fatty acid-free bovine serum albumin (BSA).

ROS Levels Determination:

Approximately $5\times10^4$ SAEC were seeded on 2-chambered culture slides in triplicate or 10,000 SAEC per well were plated in a 96-well plate. After they attached, cells were starved in basal medium containing 0.1% serum without or with fidarestat (10 μM) for overnight. Next day cells were washed with 1×HBSS buffer and incubated with 10 μM H2DCF-DA at 37° C. for 30 min, washed again to remove excess H2DCF-DA and treated with IL-13 (25 ng/ml) for 1 h. At the end of incubation, cells were washed twice with cold 1×HBSS buffer. The cells on the culture slide were mounted using floursave mounting medium with DAPI after which photomicrographs were acquired using a fluorescence microscope (Nikon). Fluorescence was determined using 485 nm excitation and 538 nm emission wavelengths for cells in 96-well plate and relative ROS production is expressed as mean fluorescence intensity (MFI) (arbitrary units).

Air-Liquid Interface Culture:

For air-liquid interface (ALI) culture, SAEC were seeded at $8.5\times10^4$ cells/12-mm-diameter PET transparent insert with 1.0 μM pores (12-well millicell culture insert; Millipore) and pre-coated with rat tail collagen type-1 (Sigma-Aldrich). The cells were grown submerged in the differentiation medium as described earlier by Zhen et al. (*Am J Respir Cell Mol Biol* 36: 244-253, 2007). The differentiation medium contained a 1:1 mixture of DMEM and small airway epithelial growth medium supplemented as described above, except that gentamycin sulfate, amphotericin B, and triiodothyronine were replaced with 1% penicillin/streptomycin, and 50 nM all-trans retinoic acid. The SAEC were maintained submerged for the first 7 days, after which the apical medium was removed and an air-liquid interface culture was established. The cells were maintained at ALI for the remainder of the culture period. Medium was refreshed every third day and once in a week the apical surface of the cells was rinsed with PBS to remove accumulated mucus and debris. Cells were maintained at 37° C. in 95% air and 5% $CO_2$ in a humidified incubator. The cells on the ALI were pre-treated with AR inhibitor, fidarestat (10 μM), for over-night from the basal side in differentiation medium without EGF beginning day 11 after establishment of ALI and stimulated with IL-13 by addition of recombinant human IL-13 (25 ng/ml) to the medium for varying time periods as indicated.

Cell Fixation and Immunocytochemistry:

After the completion of incubation with IL-13, the apical surface of the cells was rinsed with PBS and cells were fixed in 10% z-fix, aqueous buffered-zinc formalin (Anatech Ltd; Battle Creek, Mich.), for 24 h at 4° C. and embedded in paraffin. The 504 thin sections of the epithelial cell monolayer on the membrane insert were stained with H&E and periodic acid Schiff (PAS)-stain. The stained sections were analyzed and representative fields were photographed using a Photometrix CoolSNAP Fx camera mounted on a NIKON Eclipse TE 200 UV microscope. Antibodies against β-tubulin and Muc5AC (Santa Cruz Biotechnology, Santa Cruz, Calif.) and matched control IgG were used for immunocytochemistry. Antibodies were detected using the Vector LSAB kit (Vector Laboratories, Burlingame, Calif.) as suggested by the manufacturer.

RT-PCR:

Total RNA was isolated from differentiated SAEC treated with IL-13 with or without AR inhibitor by using RNeasy kit (Qiagen) as per supplier's instructions. Aliquots of RNA (1.0 μg) isolated from each sample were reverse-transcribed with Omniscript and Sensiscript reverse transcriptase one-step RT-PCR system with HotStar Taq DNApolymerase (Qiagen) at 55° C. for 30 min followed by PCR amplification. The oligonucleotide primer sequences were as follows: Muc5AC: 5'-TCCGGCCTCATCTTCTCC-3' (SEQ ID NO:1) (sense) and 5'-ACTTGGGCACTGGTGCTG-3' (SEQ ID NO:2) (Antisense); SPDEF: 5'-CGAAGTGCTCAAGGACATC-GAG-3' (SEQ ID NO:3) (sense) and 5'-CGGTATTGGT-GCTCTGTCCACA-3' (SEQ ID NO:4) (anti-sense) and GAPDH: 5'-GACCCCTTCATTGACCTCAAC-3' (SEQ ID NO:5) (sense) and 5'-CATACCAGGAAATGAGCTTG-3' (SEQ ID NO:6) (antisense). RT-PCR reaction was carried out in a PCR Sprint thermal cycler (Thermo electron corporation, Milford, Mass.) under the following conditions: initial denaturation at 95° C. for 15 min followed by 35 cycles at 94° C. for 1 min, 60° C. for 1 min, 72° C. for 1 min, followed by 72° C. for 10 min for final extension. The RT-PCR products were subjected to electrophoresis on a 1.5% agarose-1×TAE gels containing 0.5 m/ml ethidium bromide. The densitometry analysis of the gel was performed using NIH image analysis software.

Western Blot Analysis:

Subsequent to incubations, the cells were washed with cold PBS and lysed in RIPA lysis buffer. The cell lysates were pooled and cleared by centrifugation. Protein levels were determined using Bradford reagent (Biorad, Hercules, Calif.). Forty micrograms of protein were mixed with sample buffer and resolved on 10% SDS-PAGE. After electrophoresis, the proteins were electro transferred to a nitrocellulose membrane, blocked with 5% nonfat milk in TBST, and probed with antibodies against phospho-ERK1/2, ERK1/2, phospho-STAT-6, STAT-6, Muc5AC, Muc5B, and SPDEF for overnight at 4° C. The blots were then washed, exposed to HRP-conjugated secondary antibodies (1:5,000 dilution) for 1 h, and the antigen-antibody complex was detected by enhanced chemiluminescence (Amersham Pharmacia Biotech, Piscataway, N.J., USA). The membranes were stripped and reprobed with antibodies against GAPDH to depict loading control. Densitometry was performed by biospectrum 410 image system from Ultra Violate Products Ltd. (Cambridge, UK).

Muc5AC ELISA:

Muc5AC levels in the culture medium were assessed by ELISA using commercially available human anti-Muc5AC ELISA essentially as described by the manufacturer (Cosmo Bio USA; Carlsbad, Calif.).

Sensitization and Challenge of Animals:

Wild type C57BL/6 and Balb/cJ mice were purchased from Harlan Sprague-Dawley (San Diego, Calif., USA) and AR null mice on C57BL/6 background were bread by us at Animal resource center, UTMB, Galveston, Tex. Six-eight weeks old female mice were sensitized with RWE as previously described (Hwang et al., FASEB J. 19: 795-797, 2005). Briefly, mice were sensitized with two intraperitoneal administrations of 100 μl of endotoxin-free RWE (150 μg) combined with Alum adjuvant (1 mg) in a 3:1 ratio (v/v), on days 0 and 4. On day 11, mice (n=6) were challenged intranasally with RWE (100 μg). A parallel group of mice received fidarestat (7 mg/kg body wt/day) in drinking water from one day before the challenge. Control groups of mice were challenged with equivalent volumes of PBS. The animals were euthanized at different time points as mentioned, with ketamine (135 mg/kg body wt) and xylazine (15 mg/kg body wt), the lungs were perfused and fixed with 4% paraformaldehyde, embedded in paraffin, and sectioned to 5 μm. Lung sections were stained with PAS and the representative fields were observed and photographed with a Photometrix CoolSNAP Fx camera mounted on a NIKON Eclipse TE 200 UV microscope.

Determination of IL-13 in Mice Lungs:

The mice lungs were harvested 16 h after RWE-challenge and total RNA was isolated. From each sample, one microgram of total RNA was transcribed into first-strand cDNA and quantitative RT-PCR was conducted using IL-13 specific forward and reverse primers 5'AGACCAGACTCCCCTGTGCA (SEQ ID NO:7), 3'TGGGTCCTGTAGATGGCATTG (SEQ ID NO:8); GAPDH specific primers (5'TGTGTCCGTCGTGGATCTGA (SEQ ID NO:9), 3'CCTGCTTCACCACCTTCTTGAT (SEQ ID NO:10)) were used as housekeeping gene (HKG) control. Data were collected and analyzed by ABI 7000 System equipment and software (Applied Biosystems, Foster City, Calif.). To assess expression levels, delta-delta Ct method ($\Delta\Delta C_T$) was used. Values of expression in fold increase (ratio of control) were calculated using the formula for relative expression by the method of Delta Delta $C_T$ ($\Delta\Delta C_T$): $F=2^{-\Delta\Delta C}$, F=fold change (ratio of control), $-\Delta\Delta C_T=(C_T \text{ Target}-CT_{HKG})^{Time\,x}-(C_T \text{ Target}-C_{THKG})^{Time\,0}$. Time x is any time point. Time 0 represents 1× expression of the target gene normalized to a HGK.

Detection of STAT-6 Phosphorylation in Mouse Lungs:

Approximately 20 h after RWE-challenge, mice are killed, and their lungs perfused and fixed with 4% paraformaldehyde, embedded in paraffin, and 5 μm sections were obtained. The sections were immunostained with p-STAT-6 specific primary antibodies followed by probing with either FITC labeled secondary antibodies and mounted with fluorosave medium with DAPI or DAB-based HRP-conjugated antibodies from Vector LSAB kit (Vector Laboratories, Burlingame, Calif.) and counterstained with hematoxylin and eosin. Photomicrographs were acquired by a Photometrix CoolSNAP Fx camera mounted on a NIKON Eclipse TE 200 UV microscope using fluorescence or bright-field microscopy, respectively.

Statistics:

Data presented as mean±SE and statistical significance was determined by unpaired Student's t test using graph pad prism software (GraphPad Software, Inc. La Jolla, Calif.). The value of P<0.05 was considered as statistically significant.

The invention claimed is:

1. A method of treating COPD in a subject diagnosed with, exhibiting symptoms of, or at risk of developing COPD comprising administering to the subject a therapeutically effective amount of an aldose reductase inhibitor selected from the group consisting of fidarestat, epalrestat, ponalrestat, risarestat, imirestat, zopolrestat, minalrestat, ranirestat, and tolrestat.

2. The method of claim 1, wherein the subject currently smokes or previously smoked tobacco.

3. The method of claim 1, wherein the aldose reductase inhibitor is administered as a prodrug.

4. The method of claim 1, wherein the aldose reductase inhibitor is administered by inhalation or instillation.

5. The method of claim 1, wherein the aldose reductase inhibitor is administered orally.

6. The method of claim 1, wherein the aldose reductase inhibitor is fidarestat.

7. The method of claim 1, wherein the aldose reductase inhibitor is administered at a dose of 1 to 800 mg/day.

8. A method of treating COPD in a subject diagnosed with, exhibiting symptoms of, or at risk of developing COPD comprising administering to the subject a therapeutically effective amount of fidarestat.

* * * * *